(12) United States Patent
Bressan et al.

(10) Patent No.: US 8,975,303 B2
(45) Date of Patent: Mar. 10, 2015

(54) SYNTHESIS GAS METHANATION PROCESS AND APPARATUS

(75) Inventors: Luigi Bressan, Corsico (IT); Maria Sudiro, Corsico (IT)

(73) Assignee: Foster Wheeler Italiana S.r.l., Corsico (IT)

( * ) Notice: Subject to any disclaimer, the term of this patent is extended or adjusted under 35 U.S.C. 154(b) by 553 days.

(21) Appl. No.: 13/382,890

(22) PCT Filed: Jul. 8, 2010

(86) PCT No.: PCT/IB2010/001678
§ 371 (c)(1),
(2), (4) Date: Mar. 26, 2012

(87) PCT Pub. No.: WO2011/004251
PCT Pub. Date: Jan. 13, 2011

(65) Prior Publication Data
US 2012/0184632 A1    Jul. 19, 2012

(30) Foreign Application Priority Data

Jul. 8, 2009 (IT) .............................. MI2009A1211

(51) Int. Cl.
| | | |
|---|---|---|
| C07C 27/00 | (2006.01) |
| G05D 23/00 | (2006.01) |
| B01J 21/20 | (2006.01) |
| C10G 2/00 | (2006.01) |
| C01B 3/16 | (2006.01) |
| C07C 1/04 | (2006.01) |
| C10L 3/08 | (2006.01) |

(52) U.S. Cl.
CPC ... *C10G 2/30* (2013.01); *C01B 3/16* (2013.01); *C07C 1/0485* (2013.01); *C10L 3/08* (2013.01); *C01B 2203/0261* (2013.01); *C01B 2203/0283* (2013.01); *C01B 2203/0445* (2013.01); *C01B 2203/047* (2013.01); *C01B 2203/147* (2013.01); *C01B 2203/1685* (2013.01); *C01B 2203/169* (2013.01); *C10G 2300/807* (2013.01)
USPC ........... 518/712; 518/700; 518/711; 422/110; 422/208; 422/626

(58) Field of Classification Search
USPC ........... 518/700, 711, 712; 422/110, 208, 626
See application file for complete search history.

(56) References Cited

U.S. PATENT DOCUMENTS

| | | | |
|---|---|---|---|
| 3,890,113 A | 6/1975 | Child et al. ................. | 48/197 R |
| 3,967,936 A | 7/1976 | Tajbl et al. .................. | 48/197 R |
| 4,046,523 A | 9/1977 | Kalina et al. ................ | 48/197 R |
| 4,115,075 A | 9/1978 | McNamee et al. .......... | 48/197 R |
| 4,123,448 A | 10/1978 | Kleinpeter .................... | 260/449 |

OTHER PUBLICATIONS

Li et al., "CO removal by two-stage methanation for polymer electrolyte fuel cell," Journal of Natural Gas Chemistry 17(4):359-364, 2008.

*Primary Examiner* — Jafar Parsa
(74) *Attorney, Agent, or Firm* — Seed IP Law Group PLLC

(57) ABSTRACT

In a synthesis gas methanation process, at least one first fraction of synthesis gas to treat is fed, together with steam, to a shift reactor where a shift reaction occurs; the gas flow produced in the shift reactor is then fed to a first methanation reactor where a methanation reaction occurs and then to further second methanation reactors in series, where further methanation reactions, performed with the addition of fresh synthesis gas which has not been subjected to the shift reaction.

10 Claims, 1 Drawing Sheet

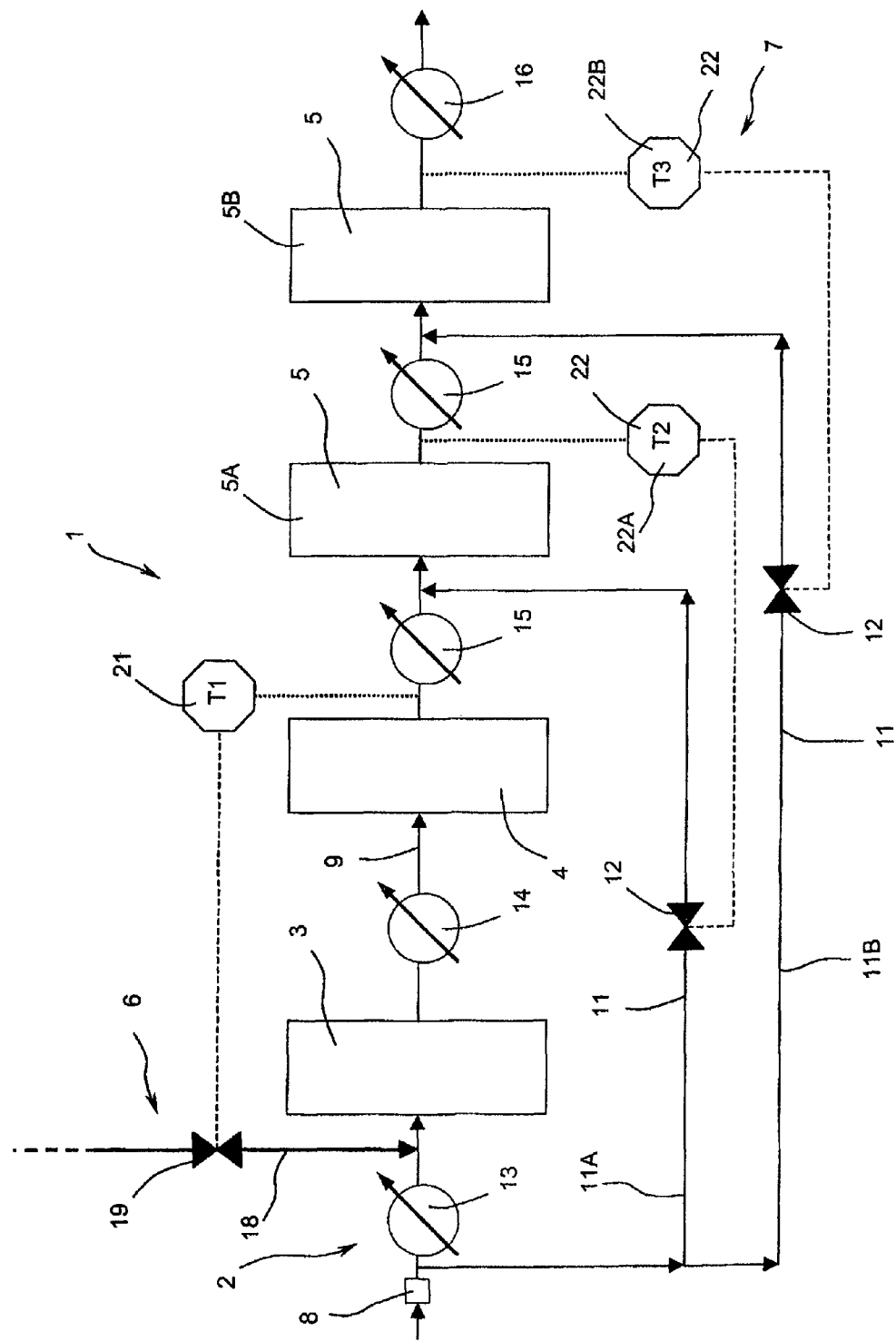

SYNTHESIS GAS METHANATION PROCESS AND APPARATUS

BACKGROUND

1. Technical Field

The present invention relates to a synthesis gas methanation process and apparatus.

2. Description of the Related Art

As is known, the term "synthesis gas" indicates a gas mixture consisting substantially of carbon monoxide (CO) and hydrogen ($H_2$) and, in smaller amounts, of carbon dioxide ($CO_2$), steam ($H_2O$) and other compounds or impurities (also depending on the source used for its production); in general, the synthesis gas is obtained by appropriate processes of oxidative gasification of different sources (such as coal, petroleum coke, biomasses, refinery oils, different kinds of wastes, residuals of the petrochemistry industry etc.)

Among the different applications of the synthesis gas, its use is known for methanation processes, in which the synthesis gas is substantially used to produce methane.

The methanation reaction implies the reaction of $H_2$ and CO in a molar ratio of 3:1. This reaction is performed on a catalyst and is very fast and exothermic. This is why an accurate control of the exothermicity of the reaction may be needed to have an overall feasible and efficient process.

Processes are known in which the methanation reaction is performed in a methanation reactor fed with a mixture having a molar ratio of $H_2$:CO equal to 3:1 and is accompanied by a flow of inert matter (i.e., matter only marginally involved in the reaction) to mitigate the thermal effect of the development of reaction heat. The flow of inert matter is obtained in particular by recirculating part of the end product of the reaction to the methanation reactor with the aid of a compressor. The need to employ a compressor (generally having considerable size and a high energetic consumption) negatively affects the overall efficiency and the reliability of the process.

Furthermore, in this kind of processes the synthesis gas employed must be produced or in any case treated so as to have the desired composition and specifically the cited molar ratio $H_2$:CO, obtained for example by partial or complete shift reaction and $CO_2$ removal.

BRIEF SUMMARY

One or more embodiments of the present invention may provide a synthesis gas methanation process and apparatus that allow an accurate control of the methanation reaction in a simple and fully effective manner.

One or more embodiments of the invention provides a method and apparatus for controlling the high exothermicity of the methanation reactions without recurring to heavy recirculation or other complicated solutions. In one embodiment, control of the methanation reaction is carried out by introducing in the corresponding methanation reactors flows having a high content of inert, obtained in a preliminary shift step with the addition of steam; as well as by feeding fractions of fresh synthesis gas (which has not passed through the shift reactor) in the possible following methanation reactors.

BRIEF DESCRIPTION OF THE DRAWING

Further features and advantages of the present invention will become apparent from the following disclosure of a non limitative example, with reference to the accompanying FIGURE which is a diagrammatic view of a synthesis gas methanation apparatus made according to the invention.

In the accompanying FIG. 1, indicates as a whole a synthesis gas methanation apparatus.

DETAILED DESCRIPTION

Apparatus 1 comprises a gas feeding circuit 2, a shift reactor 3 (in which a shift reaction occurs), a first methanation reactor 4 and one or more subsequent second methanation reactors 5 (in which respective methanation reactions occur), a steam feed circuit 6, and a control system 7 operatively connected to gas feed circuit 2 and to steam feed circuit 6.

Gas feed circuit 2 has a primary inlet 8 by means of which the synthesis gas is fed to apparatus 1; primary inlet 8 is connected for example to a gasification apparatus of any known type (neither shown nor disclosed for simplicity); the synthesis gas fed to apparatus 1 by means of primary inlet 8 is a generic synthesis gas, therefore essentially consisting of $H_2$, CO, $CO_2$, $H_2O$ and obtained from any partial oxidation process of carbon, petroleum coke, biomasses, refinery oil and residuals of petrochemical industry in general, solid urban waste, etc.; advantageously (but not necessarily), the synthesis gas fed to apparatus 1 has been preliminarily cleaned in a (known) appropriate purification stage, although it has not been subjected to treatments to adjust the $H_2$/CO molar ratio.

It should in any case be understood that the purification stage may also be placed downstream of shift reactor 3 (in particular, between the latter and first methanation reactor 4) depending on the features of the shift catalyst used in shift reactor 3 for the shift reaction and specifically on the fact that such a catalyst can resist the impurities contained in the synthesis gas employed.

Primary inlet 8 is connected to a primary line 9 of gas feed circuit 2; shift reactor 3 and methanation reactors 4, 5 are arranged in series along primary line 9, with methanation rectors 4, 5 arranged in series one with respect to the other and downstream of shift reactor 3 along primary line 9.

In general, apparatus 1 comprises at least first methanation reactor 4 and one or more second subsequent methanation reactors 5. In the preferred embodiment shown in the accompanying FIG. 1, apparatus 1 comprises first methanation reactor 4 and two subsequent methanation reactors 5A, 5B, i.e., overall three methanation reactors in series, to which the present disclosure will refer to hereinafter; it should be understood that apparatus 1 may comprise a different number of second subsequent methanation reactors 5 (for example, even only one or more than two).

Gas feed circuit 2 also comprises one or more auxiliary lines 11 which connect primary inlet 8 to respective inlets of the subsequent methanation reactors 5; in the example shown, two auxiliary lines 11A, 11B take fresh synthesis gas (i.e., synthesis gas that has not passed through shift reactor 3) from primary inlet 8 to each of methanation reactors 5A, 5B.

Auxiliary lines 11 are provided with respective flowrate adjustment groups 12, for example valve groups, controlled by control system 7.

Gas feed circuit 2 is also provided along primary line 9 with a heat exchanger 13 arranged upstream of shift reactor 3, with a heat exchanger 14 arranged upstream of first methanation reactor 4, with other heat exchangers 15 arranged upstream of each subsequent methanation reactor 5, as well as, optionally, with a final heat exchanger 16 downstream of last methanation reactor 5B.

All heat exchangers 13, 14, 15 are arranged along primary line 9 upstream of a respective shift reactor 3 or of a methanation reactor 4, 5 to cool the gas flows entering each of these reactors.

Auxiliary lines 11, engage primary line 9, at the inlet of respective second methanation reactors 5, downstream of respective heat exchangers 15.

Shift reactor 3 is configured so as to be fed with synthesis gas and steam and perform a water-gas shift reaction, i.e., a reaction in which carbon monoxide reacts with water (steam) to form carbon dioxide and hydrogen:

$$CO+H_2O \rightarrow CO_2+H_2$$

Each of methanation reactors 4, 5 is configured so as to produce methane by means of at least one methanation reaction in which carbon monoxide reacts with hydrogen to form methane and water:

$$3\,H_2+CO \rightarrow CH_4+H_2O$$

For this purpose, methanation reactors 4, 5 are provided with appropriate catalysts that can catalyze the indicated methanation reaction. Methanation reactors 4, 5 can be of different kinds and can contain one or more catalytic beds, which may have an adiabatic profile, an isothermal profile or any combination of the two profiles. The same methanation reactor may also be formed by several catalytic beds.

In first methanation reactor 4, the development of the methanation reaction passes through the decomposition of $CO_2$ by shift equilibrium, promoting the control of the exothermicity in addition to the action performed by the steam. In second methanation reactors 5, the methanation reaction is controlled by the preponderant mass of inerts.

Steam feed circuit 6 comprises a steam inlet line 18 which preferably connects to primary line 9 upstream of shift reactor 3, so that shift reactor 3 is fed with synthesis gas from primary inlet 8 and with steam from steam feed inlet 6. Steam inlet line 18 is provided with a flowrate adjustment group 19, for example a valve group, controlled by control system 7.

Advantageously, steam feed circuit 6 also connects heat exchangers 13-16, so that the steam fed to shift reactor 3 is advantageously totally or partially produced by heat exchangers 13-16.

Optionally, gas feed circuit 2 and/or steam feed circuit 6 are provided with circulation means, which are known and not shown for simplicity.

Control system 7 comprises temperature controllers 21, 22 associated to respective adjustment groups 19, 12 and configured so as to detect (by means of appropriate temperature sensors) the temperature of the gas flow circulating in gas feed circuit 2 in predetermined positions, in particular along primary line 9 at the outlet of each methanation reactor 4, 5, and accordingly to control associated adjustment groups 19, 12.

In particular, first controller 21 detects the temperature of the gas flow at the outlet of first methanation reactor 4 and controls adjusting group 19 of steam inlet line 18 for adjusting the flowrate of steam that is fed to shift reactor 3.

Other controllers 22 detect the gas flow temperature at the outlet of each methanation reactor 5 and control adjustment groups 12 of auxiliary lines 11 for adjusting the fresh synthesis gas flowrate (which has not passed through shift reactor 3) which is fed to respective methanation reactor 5.

An operation of apparatus 1 for performing the synthesis gas methanation process according to one embodiment of the invention is the following.

A first fraction of the synthesis gas to treat (for example coming from a generic gasification apparatus and from which the main impurities have simply been removed), after passing in heat exchanger 13, is fed to shift reactor 3 by means of primary line 9, together with a steam flowrate fed through steam inlet line 18.

Other synthesis gas fractions are instead drawn through auxiliary lines 11.

The amount of steam fed to shift reactor 3 is adjusted by controller 21, on the basis of the temperature of the gas flow detected at the outlet of first methanation reactor 4. The amount of steam fed to shift reactor 3 depends, as well as on the composition of the synthesis gas to treat, also on the number of second methanation reactors 5 of apparatus 1. In general, the lower is this number, the greater is the amount of steam to add.

Controller 21 adjusts the flowrate of steam fed to shift reactor 3, operating on adjustment group 19, on the basis of the temperature of the gas flow detected at the outlet of first methanation reactor 4. In particular, controller 21 operates so as to maintain temperature T1 at the outlet of first methanation reactor 4 at a value compatible with the desired equilibrium and with the features of the catalyst employed in first methanation reactor 4; accordingly, controller 21 adjusts the flow of steam to shift reactor 3 so as to ensure that shift reactor 3 is fed with an amount of steam to be used for the shift reaction and with an additional amount of steam to be used to control the exothermicity of the methanation reaction in first methanation reactor 4 (in which the steam acts as an inert and mitigates the exothermicity of the methanation reaction).

The shift reaction between carbon monoxide present in the synthesis gas and steam present in the synthesis gas and fed from outside occurs in shift reactor 3. The shift reaction reduces the content of CO of the gas flow that subsequently feeds first methanation reactor 4, and also produces an amount of $CO_2$ that acts, in the following methanation reactions, both as inert (i.e., a material that takes no part in the methanation reaction) and as secondary reagent in the methanation reaction, so as to limit the exothermicity of the methanation reactions; also the residual of $H_2O$ of the shift reaction (performed in excess of $H_2O$) that remains in the gas flow fed to first methanation reactor 4 increases the amount of inert and contributes to mitigating the methanation reaction in this reactor.

Substantially, a gas mixture compatible with a methanation reaction controlled in first methanation reactor 4 is prepared in shift reactor 3.

The gas flow coming out from shift reactor 3 is therefore cooled in heat exchanger 14 and entirely conveyed in first methanation reactor 4, where the methanation reaction occurs. The exothermicity of the methanation reaction is mitigated by the presence of considerable amounts of $CO_2$ and $H_2O$.

The gas flow coming out from first methanation reactor 4 is fed entirely to subsequent methanation reactors 5 in series.

After having been cooled in heat exchanger 15, the gas flow coming out from first methanation reactor 4 is conveyed to subsequent methanation reactor 5A, together with a fraction of the fresh synthesis gas drawn through auxiliary line 11A. The flowrate of fresh synthesis gas added to the gas flow coming out from first methanation reactor 4 and fed to methanation reactor 5A is adjusted by controller 22A on the basis of the temperature of the gas flow detected at the outlet of methanation reactor 5A. Controller 22A operates so as to maintain this temperature at a value T2 compatible with the desired equilibrium and with the features of the catalyst employed in methanation reactor 5A.

Similarly, the gas flow coming out from methanation reactor 5A passes through heat exchanger 15 and then in subsequent methanation reactor 5B, with or without the addition of another fraction of fresh synthesis gas drawn through auxiliary line 12A. The flowrate of fresh synthesis gas fed to methanation reactor 5B is adjusted by controller 22B on the basis of the temperature of the gas flow detected at the outlet of methanation reactor 5B. Controller 22B operates so as to maintain this temperature at a predetermined value T3 which is the equilibrium value of the whole system.

The methanation reaction occurring in methanation reactors 5 are also performed in excess of hydrogen so as to substantially exhaust the available carbon monoxide and in the presence of appropriate amounts of inerts ($CO_2$ and $H_2O$) which have the effect of controlling the exothermicity of the methanation reactions.

The gas flow coming out from methanation reactor 5B is a flow with a high content of methane which, appropriately cooled in heat exchanger 16, is available for different applications.

It should finally be understood that further modifications and variants which do not depart from the scope of the appended claims may be made to the process and apparatus disclosed and shown herein.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A method comprising:
providing steam and a first fraction of synthesis gas to a shift reactor, wherein a shift reaction occurs to produce a shift reaction gas;
providing the shift reaction gas to a first methanation reactor, wherein a methanation reaction occurs to produce a first methanation reaction gas;
providing the first methanation reaction gas to at least one second methanation reactor;
providing a flow of synthesis gas that has not been through the shift reactor to the second methanation reactor, wherein a methanation reaction occurs to produce a second methanation reaction gas;
removing the second methanation reaction gas from each of the second methanation reactors through an outlet, wherein the flowrate of the synthesis gas provided to each second methanation reactor is adjusted as a function of the temperature of the second methanation reaction gas flow detected at the outlet of the same methanation reactor; and
adjusting the amount of steam provided to the shift reactor as a function of the temperature of the first methanation reaction gas flow detected at an outlet of the first methanation reactor.

2. The method according to claim 1, further comprising removing the shift reaction gas from an outlet of the first methanation reactor, wherein substantially all of the shift reaction gas that was removed from the outlet of the first methanation reactor is provided to at least one of the second methanation reactors.

3. The method according to claim 1, wherein the steam provided to the shift reactor includes a first amount sufficient to cause the shift reaction to occur and a second amount to control the exothermicity of the methanation reaction in the first methanation reactor.

4. The method according to claim 1, wherein the shift reaction reduces the CO content of the shift reaction gas and produces an amount of $CO_2$ that acts, in the first and second methanation reactors, as a reagent and as an inert for containing the exothermicity of the methanation reactions, together with a $H_2O$ residual of the shift reaction.

5. The method according to claim 1, wherein the shift reaction is performed in excess of $H_2O$.

6. The method according to claim 1, further comprising cooling at least one of the first fraction of synthesis gas provided to the shift reactor and the synthesis gas provided to one or more second methanation reactors.

7. The method according to claim 6, wherein the cooling the first fraction of synthesis gas produces at least part of the steam provided to the shift reactor.

8. A synthesis gas methanation apparatus comprising:
a shift reactor connected in fluid communication to a primary line of a gas feed circuit and to a steam feed circuit, the shift reactor being configured to receive synthesis gas via the primary line, to receive steam via the steam feed circuit, and to perform a shift reaction to produce a shift reaction gas;
a first methanation reactor arranged downstream along the primary line from and in fluid communication with the shift reactor, the first methanation reactor being configured to receive the shift reaction gas and to produce a first methanation reaction gas;
one or more second methanation reactors, each arranged along the primary line and coupled in fluid communication in series from one another downstream of the first methanation reactor, with one of the second methanation reactors being coupled in fluid communication with the first methanation reactor; and
one or more auxiliary lines coupled to the gas feed circuit and to respective second methanation reactors, the gas feed circuit being configured to provide the respective second methanation reactors with synthesis gas that do not pass through the shift reactor, the auxiliary lines include respective flowrate controls that are configured to be adjusted by a control system, the flowrate being adjusted as a function of temperature values detected at an outlet of each second methanation reactor;
a control system operatively connected to the gas feed circuit and to the steam feed circuit; and
temperature controllers associated with respective flow controls and configured to detect the temperature of the gas flow circulating in the gas feed circuit in predetermined positions along the primary line, wherein the temperature controllers detect the temperature of gas flowing at an outlet of the first methanation reactor and causes the flow control to adjust the flowrate of steam that is provided to the shift reactor.

9. The apparatus according to claim 8, comprising heat exchangers arranged along the primary line upstream at least one of the shift reactor and a respective methanation reactor, the heat exchangers being configured to cool the gas provided to the respective reactor.

10. The apparatus according to claim 9, wherein the heat exchangers are connected to the steam feed circuit and produce at least part of the steam provided to the shift reactor.

* * * * *